United States Patent [19]

Holtzman

[11] Patent Number: 4,889,692
[45] Date of Patent: Dec. 26, 1989

[54] DISPOSABLE SAMPLE PREPARATION CONTAINER

[76] Inventor: Marc E. Holtzman, 331 Trailside Way, Ashland, Mass. 01721

[21] Appl. No.: 240,984

[22] Filed: Sep. 6, 1988

Related U.S. Application Data

[63] Continuation of Ser. No. 826,471, Feb. 5, 1986, abandoned, which is a continuation-in-part of Ser. No. 668,449, Nov. 5, 1984, abandoned.

[51] Int. Cl.$^4$ .................. G01N 21/11; G01N 33/48
[52] U.S. Cl. ........................... 422/102; 422/67; 422/100; 422/103; 73/863.33; 73/863.73
[58] Field of Search ............... 422/99, 100, 102, 103, 422/61, 67; 73/863.33, 863.71, 863.72, 863.73

[56] References Cited

U.S. PATENT DOCUMENTS

| | | | |
|---|---|---|---|
| 3,111,849 | 11/1963 | Broerman | 73/863.71 |
| 3,222,135 | 12/1965 | Ashmead | 422/103 |
| 3,504,376 | 3/1970 | Bednar et al. | 422/67 X |
| 3,540,585 | 11/1970 | Rochte et al. | |
| 3,583,232 | 6/1971 | Isreeli et al. | 422/103 X |
| 3,913,790 | 10/1975 | Seidez | 422/100 |
| 3,918,913 | 11/1975 | Stevenson et al. | |
| 3,960,493 | 6/1976 | Zindler et al. | |
| 4,237,096 | 12/1980 | Popoff et al. | 422/102 |
| 4,344,768 | 8/1982 | Parker et al. | |
| 4,443,408 | 4/1984 | Mintz | 422/102 |
| 4,444,066 | 4/1984 | Ogle et al. | 73/863.72 |
| 4,576,054 | 3/1986 | Labis | 73/863.31 |
| 4,585,623 | 4/1986 | Chandler | |

FOREIGN PATENT DOCUMENTS 3201691 9/1983 Fed. Rep. of Germany ...... 422/102

Primary Examiner—Barry S. Richman
Assistant Examiner—Lynn M. Kummert
Attorney, Agent, or Firm—Nolte, Nolte & Hunter

[57] ABSTRACT

A disposable container in which samples can be routinely prepared for analysis. The container has a generally cylindrical magazine containing a plurality of open top sample preparation chambers, each of which is provided with an inlet/outlet port at the bottom, thereof; and a distributor valve beneath the magazine. Channels are provided in the top of the valve, extending between openings in the top of the valve, so that each channel provides fluid flow communication between the ports of the chambers located above the openings in the channel. The valve and magazine can be rotated relative to one another about the central axis of the magazine, so that the openings in the channels can be located beneath the ports of different combinations of chambers to provide fluid flow communication between different chambers.

25 Claims, 3 Drawing Sheets

DISPOSABLE SAMPLE PREPARATION CONTAINER

CROSS-REFERENCE TO RELATED APPLICATION

This application is a continuation of application Ser. No. 826,471, filed 2/5/86 now abandoned which is a continuation-in-part of appln Ser. No. 668,449 filed 11/5/84, (now abandoned).

BACKGROUND OF THE INVENTION

This invention relates to a disposable container in which samples can be prepared automatically or semi-automatically for analyses, such as the analyses of: blood or plasma samples for biomedical research or routine testing; pharmaceutical samples for production or research purposes; and more generally, samples requiring, for example, a plurality of routine chemical and/or mechanical treatments before analyses. This invention also relates to a method of preparing a sample for analysis in the disposable container.

Apparatus are known for facilitating the routine preparation by hand of samples for analyses. Typically, such apparatus have included a plurality of chambers for holding samples and chemical reagents and for mixing them together. See, for example, U.S. Pat. Nos. 3,913,790 and 4,237,096. However, such apparatus have not been adapted for automatically or semi-automatically preparing samples for analyses.

Apparatus are also known for automatically or semi-automatically preparing precisely measured and treated samples and delivering the samples to analysis equipment, such as liquid chromatographic equipment, See, for example, U.S. Pat. Nos. 4,366,119, 4,363,782, 4,344,768, 3,929,411 and 3,860,393. However, such sample preparation apparatus have generally had to utilize relatively complicated means to conveying samples between various locations in the apparatus where different chemical and/or mechanical treatments are carried out before the samples are analyzed. This need to convey samples between various locations has inevitably made such apparatus more expensive to construct and operate. Ways have been sought, therefore, for simplifying and reducing the automatic or semi-automatic movement of samples within such apparatus.

SUMMARY OF THE INVENTION

In accordance with this invention, a disposable container is provided, which comprises:

a magazine having a plurality of sample preparation chambers therein spaced about a vertical axis of the magazine; each chamber having a mouth at its top and an inlet/outlet port at its bottom; and a distributor valve beneath the magazine; the valve having in the top thereof at least one fluid flow communication channel that extends between at least two openings in the top of the valve; each opening in the top of the valve being adapted to establish fluid flow communication between the channel and one of the ports of the chambers when the opening is located beneath the one port; the valve and the magazine being rotatable relative to one another about the axis of the magazine, so that the openings in the top of the valve can be located beneath the ports of different combinations of chambers to provide fluid flow communication between such different combinations of chambers through the channel.

This container can provide simplified movement of a sample between its chambers wherein different chemical and/or mechanical operations can be carried out to prepare the sample of analysis. The container also lends itself to the automation of routine sample preparations.

BRIEF DESCRIPTION OF THE DRAWINGS

FIG. 4 shows the top surface of a distributor valve within the container of this invention; portions of the top surface of the valve have been cut away to show channels in the top of the valve that can provide fluid flow communication between chambers in the magazine which are shown in phantom.

DETAILED DESCRIPTION OF THE PREFERRED EMBODIMENTS

Figure 1:
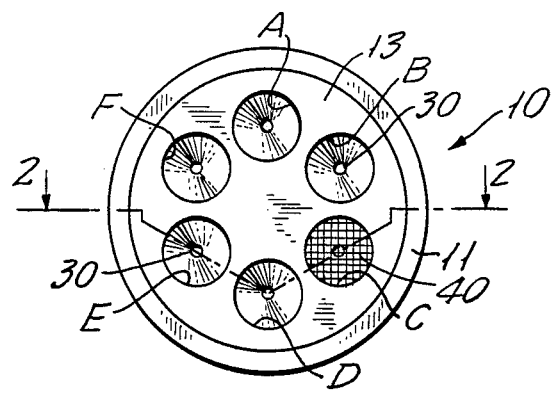
FIG. 1 is a schematic top plan view of a disposable container of this invention, showing a magazine within the container that has a plurality of open-mouth sample preparation chambers therein.

FIGS. 1–4 show a disposable, generally cylindrical, sample preparation container of this invention, generally 10. The container 10 comprises a generally cylindrical, outer housing 11 having a generally circular opening 12 at the top thereof. Provided within the housing 11 is a generally cylindrical magazine 13 that has its central vertical axis coinciding with the central vertical axis of the housing 11. Equally spaced about the central vertical axis of the magazine 13 are a plurality of generally cylindrical, vertically aligned, sample preparation chambers A, B, C, D, E and F which are each open at the top. The magazine 13 fits closely within the housing 11 and is preferably adapted to be inserted into the housing 11 through its opening 12 at the top. Mating male and female detent members 14 are provided between the upstanding, generally cylindrical walls of the housing 11 and magazine 13 to position and retain the magazine within the housing, so that the magazine cannot rotate within the housing about its central vertical axis and cannot move outwardly of the housing 11 through the opening 12. Of course, other means for positioning and retaining the magazine 13 in the housing 11 can be used such as a threaded mating of the housing and magazine, pin locks, etc.

Figure 2:
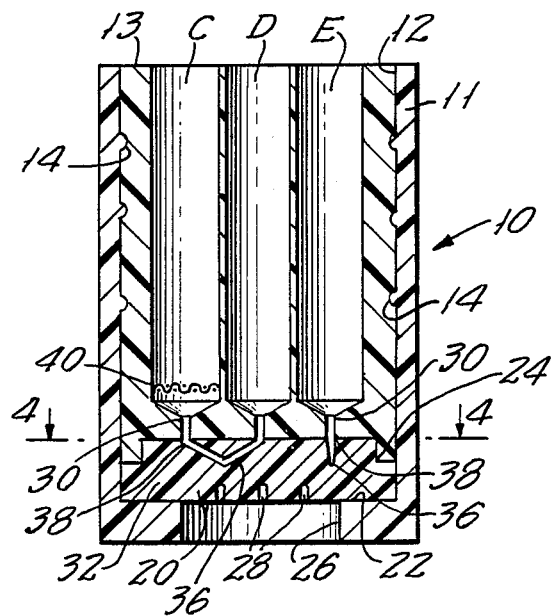
FIG. 2 is a schematic sectional view taken along line 2—2 of FIG. 1.
Figure 3:
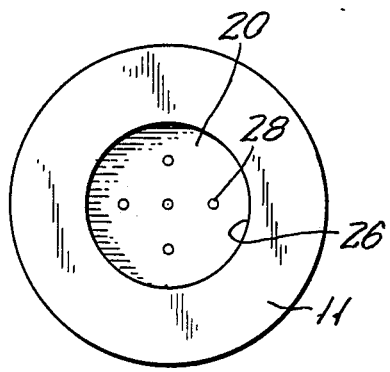
FIG. 3 is a schematic bottom plan view of the container of FIGS. 1 and 2.
Figure 4:
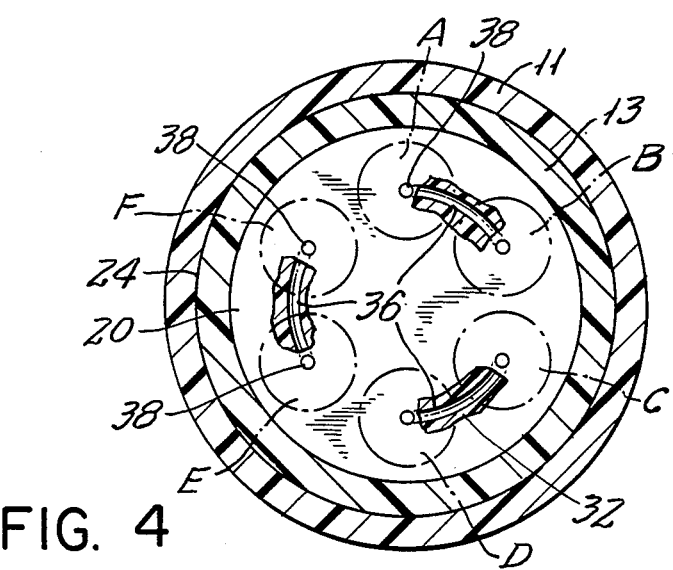
FIG. 4 is a schematic sectional view taken along line 4—4 in FIG. 2.

As shown in FIGS. 2 and 4, a rotary distributor valve 20 is also provided in the housing 11 of container 10, beneath the magazine 13 and atop a generally annular, inwardly extending ledge 22 on the bottom of the housing 11. The top of the valve 20 is closely mated to the bottom of the magazine 13, and juxtaposed annular stepped members 24 in the valve and magazine permit the valve to be rotated relative to the magazine within the housing 11 about the central vertical axis of the magazine. The valve 20 fits closely within the housing 11 and closely beneath the magazine 13 and preferably is adapted to be inserted into the housing through its opening 12 at the top thereof. As shown in FIGS. 2 and 3, a generally circular aperture 26, surrounded by the ledge 22, is provided in the bottom of the housing 11. The aperture 26 allows access to a plurality of key receptors 28 in the bottom of the valve 20 which can be used for grasping the bottom of the valve 20 so that the valve can be rotated about the central vertical axis of the magazine 13 while the housing 11 and magazine are held against rotation.

At the bottom of each chamber A-F in the magazine 13 is an inlet/outlet port 30 as shown in FIGS. 1 and 2. Each port 30 extends vertically downward from the bottom of each chamber A-F through the bottom of the magazine 13. At the top of each chamber A-F in the magazine 13 is an open mouth 31 through which liquids and solids can be introduced into the chamber.

Provided in the top of the rotary valve 20 are means, generally 32, for providing fluid flow communication between the ports 30 of the chambers A-F. As shown in FIGS. 2 and 4, the fluid flow communication means 32 preferably comprises a plurality of channels 36 in the top of the valve 20. At the ends of each channel 36 are a pair of openings 38 in the top of the valve 20. The pair of openings 38 in each channel 36 can be disposed beneath the ports 30 of a pair of chambers A-F, that are adjacent to one another about the central vertical axis of the magazine, to establish fluid flow communication through the channel 36 between the ports 30 of the pair of adjacent chambers A-F. For example, the openings 38 in the channels 36 in the valve 20 in their positions in FIG. 4 are adapted to provide fluid flow communication through the channels 36 between the ports 30 of the following pairs of chambers: A and B, C and D, and E and F. The key receptors 28 can be used to rotate the valve 20 about the central vertical axis of the magazine 13 so that different pairs of chambers A-F are in fluid flow communication through the channels 36 in the valve 20. For example, the valve 20 can be rotated clockwise 60° from its position in FIG. 4 so that the following different pairs of chambers are in fluid flow communication through the channels 36: B and C, D and E, and F and A.

The container 10 of this invention and its housing 11, magazine 13 and valve 20 can be made of any conventional metal, glass and/or plastic materials. Preferably, the container 10 and its parts are made of a relatively strong but resilient plastic which is chemically inert to any reagents, with which they will come into contact. In this regard, the container 10 is preferably made of a relatively inexpensive plastic material, such as high density polyethylene or nylon, so that it can be suitably disposed of after being used for one complete preparation of a sample for analysis.

Although the valve 20 can be rotated manually relative to the magazine 13, the valve 20 is especially adapted to be rotated by conventional automatic means which fit into the key receptors 28 in the bottom of the valve and rotate the key receptors about the central vertical axis of the magazine 13. As a result, the container 10 of this invention can be used to completely automate the routine preparation of a sample prior to its analysis. In this regard, the valve 20 can be rotated automatically to move automatically the channels 36 beneath the ports 30 of different pairs of chambers A-F at different times so as to provide communication between different combinations of chambers A-F at different times depending upon, for example: (a) the kinds of chemical and/or mechanical treatments which are to be automatically carried out within the different chambers A-F upon a sample; and (b) the sequence of such treatments which are to be automatically carried out upon the sample.

If desired, the juxtaposed bottom of the magazine 13 and top of the valve 20 can be provided with means (not shown) for indicating that the valve 20 has been rotated to a position, relative to the magazine 13, where the inlet/outlet ports 30 of the chambers A-F are vertically aligned with the openings 38 at the ends of the channels 36 in the top of the valve 20. Such means can comprise a plurality of mating male and female detent members (not shown) which: (a) are located on the juxtaposed surfaces of the magazine 13 and valve 20 about the central vertical axis of the magazine; (b) mate only when the openings 38 are beneath the ports 30; and (c) restrain but do not effectively prevent the valve 20 from being rotated relative to the magazine 13.

If desired, the top of the magazine 13 can be provided with means (not shown) for indicating the position of the specific chambers A-F in the magazine about its central vertical axis. Such means can comprise one or more upstanding projections (not shown) on top of the magazine 13 between one or more specific chambers A-F.

In accordance with this invention, the container 10 can be used with automatic or semi-automatic sample preparation equipment (not shown) which can: (a) deposit a sample and/or solvents within the chambers A-F through their open mouths 31; (b) urge the samples and solvents to move between the chambers A-F through their inlet/outlet ports 30 and through the openings 38 and channels 36 in the top of the valve 20; (c) subject the samples and solvents to various chemical and/or mechanical treatments within the chambers A-F; and/or (d) remove the samples, after they have been treated with the solvents and subjected to chemical and/or mechanical treatment, from the chambers A-F for analysis. For example, a conventional filter 40 can be automatically provided within chamber C of the container 10 as shown in FIG. 2; then, a liquid sample can be automatically provided in chamber C above the filter 40; and then the sample can be urged automatically to flow downwardly through the filter 40 and through one of the channels 36 into chamber D. In this regard, a disposable plunger (not shown) can be automatically provided on top of chamber C and then urged inwardly of chamber C, to urge the liquid sample to flow through the filter 40 and into chamber D, after the liquid sample has been provided in chamber C. Following such a filtration step, the liquid sample in chamber D can be automatically subjected to, for example, a liquid-liquid extraction, after which the extract can be urged automatically to flow, for example, to chamber E in container 10 by automatically rotating valve 20 clockwise 60° from its position in FIG. 4 and automatically urging another disposable plunger inwardly of chamber D. A plurality of the containers 10 holding different samples can also be provided on a rotating carousel (not shown) that is located beneath such automatic or semi-automatic sample preparation equipment and that can automatically or semi-automatically position the containers 10 beneath the different pieces of such equipment for treatment at different times so that each piece of equipment can, if desired, perform its chemical or mechanical treatment upon the samples in the chambers A-F of each container 10 on the carousel at different times, depending upon the type and sequence of treatments to be used for preparing each sample. Thus, it can be seen that the container 10 of this invention can be used to prepare routine samples for analysis, using automated equipment and techniques. The container 10 can thereafter be disposed of, so that the danger of cross-contamination between samples, being analyzed, is virtually eliminated. However, the container 10 can, if desired, be cleaned and reused after each sample preparation.

Figure 5:
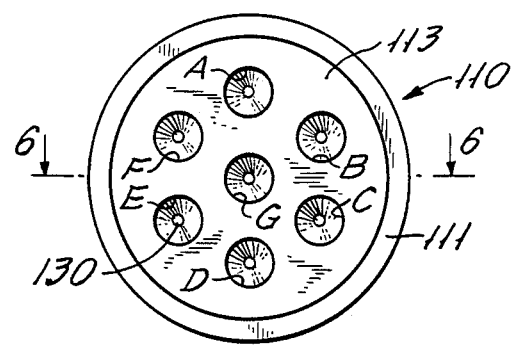
FIG. 5 is a schematic top plan view, like FIG. 1, of an alternative embodiment of the container of this invention.
Figure 6:
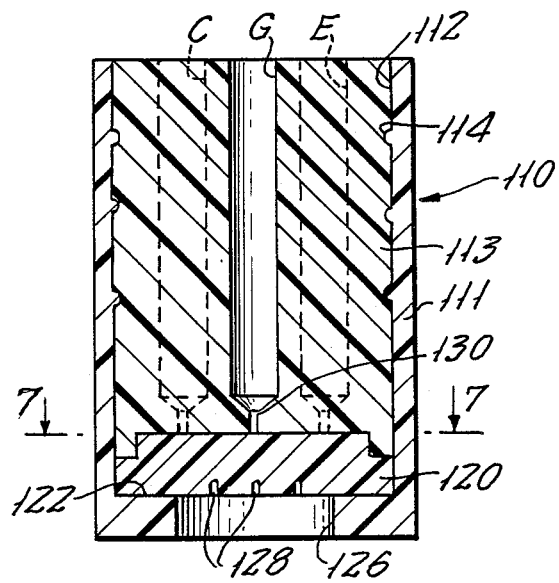
FIG. 6 is a schematic sectional view, similar to FIG. 2, taken along line 6—6 in FIG. 5.
Figure 7:
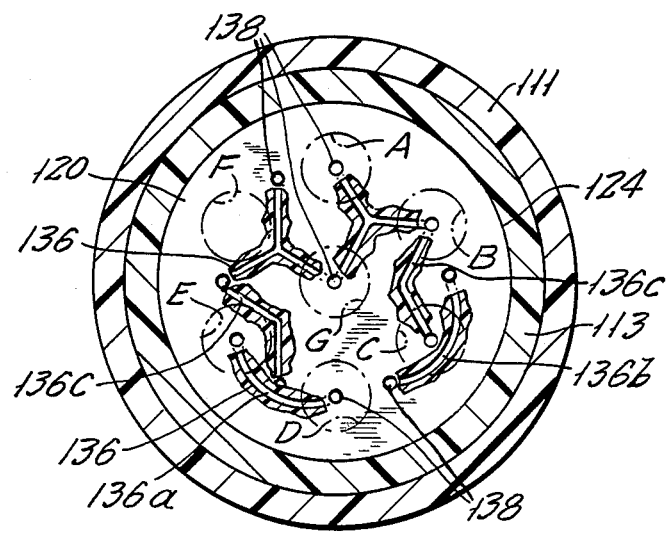
FIG. 7 is a schematic sectional view, similar to FIG. 4, taken along line 7—7 in FIG. 6.

FIGS. 5-7 show a disposable, generally cylindrical, sample preparation container, generally 110, in accordance with an alternative embodiment of this invention. The container 110 has a generally cylindrical magazine 113 within a generally cylindrical, outer housing 111. Mating male and female detent members 114 are provided between the walls of the housing 111 and magazine 113. A rotary distributor valve 120 is within the housing 111 beneath the magazine 113 and atop a generally annular ledge 122 at the bottom of the housing. The bottom of the valve 120 has a plurality of key receptors 128 which are accessible through an aperture 126 in the bottom of the housing 111 and which can be used for rotating the valve within the housing about the central vertical axis of the magazine 113, while holding the housing and magazine against rotation. The container 110 of FIGS. 5-7 is, in all essential respects, like the container 10 of FIGS. 1-4, except the container 110 has an additional, generally cylindrical, vertically aligned, sample preparation chamber G at the center of its magazine 113 and has three different channels, generally 136, in the top of the valve 120. In this regard, two channels 136a and 136b only have openings 138 in the top of the valve 120 at their ends. These two channels 136a and 136b are adapted to provide fluid flow communication only between the inlet/outlet ports 130 at the bottom of adjacent chambers, such as chambers D and E in FIG. 7 which have their ports 130 located directly above the openings 138 at the ends of one of these channels 136a. The third channel 136c has openings 138 both between and at its ends. This channel 136c can provide fluid flow communication between the ports 130 of a plurality of chambers, such as chambers A, B, C and G in FIG. 7 having their ports 130 located above the openings 138 in the channel 136c. As shown in FIG. 7, chamber F is not in fluid flow communication with the other chambers. The key receptors 128 can be used to rotate the valve 120 about the central vertical axis of the magazine 113 so that different chambers A-G are in fluid flow communication through the channels 136 in the top of the valve 120. For example, the valve 120 can be rotated clockwise 30° from its position in FIG. 7 so that: adjacent chambers C and D are in fluid flow communication through the channel 136b; chambers A, E, F and G are in fluid flow communication through the third channel 136c, and chamber B is not in fluid flow communication with the other chambers.

Figure 8:
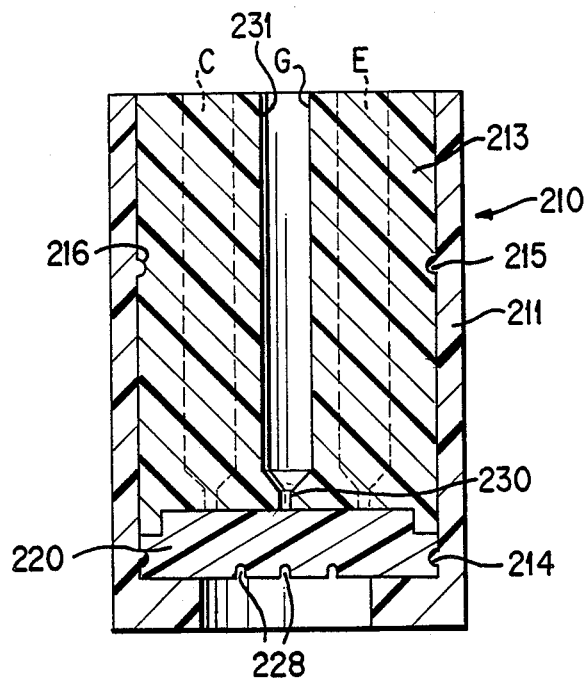
FIG. 8 is a schematic sectional view, similar to FIG. 6, of another alternative embodiment of the container of this invention.

FIG. 8 shows a disposable, generally, cylindrical, sample preparation container, generally 210, in accordance with another alternative embodiment of this invention. The container 210 of FIG. 8 is, in all essential respects, like the container 110 of FIGS. 5-7, except the container 210 has: (a) mating male and female detent members 214 provided between the upstanding, generally cylindrical walls of the housing 211 and the rotary distributor valve 220 to position and retain the valve 220 within the housing 211 so that the valve cannot rotate within the housing about its central vertical axis; and (b) an annular key 215 and mating keyway 216 in the generally cylindrical walls of the housing 211 and magazine 213, respectively, to retain the magazine within the housing but allow the magazine to rotate within the housing about its central vertical axis. Key receptors 228 on the bottom of the valve 220 can be used for grasping and holding the bottom of the valve so that the valve and housing 211 do not rotate about the central vertical axis of the housing when the magazine is rotated about its central vertical axis. Thus, the magazine 213 and the valve 220 can be rotated relative to one another about the axis of the magazine by rotating the magazine and simultaneously grasping the key receptors 228 of the valve 220 to prevent them from rotating, whereby the openings in the top of the valve can be provided beneath the inlet/outlet ports 230 of different combinations of chambers A-G to provide fluid flow communication between such different combinations of chambers through the channels in the valve.

Figure 9:
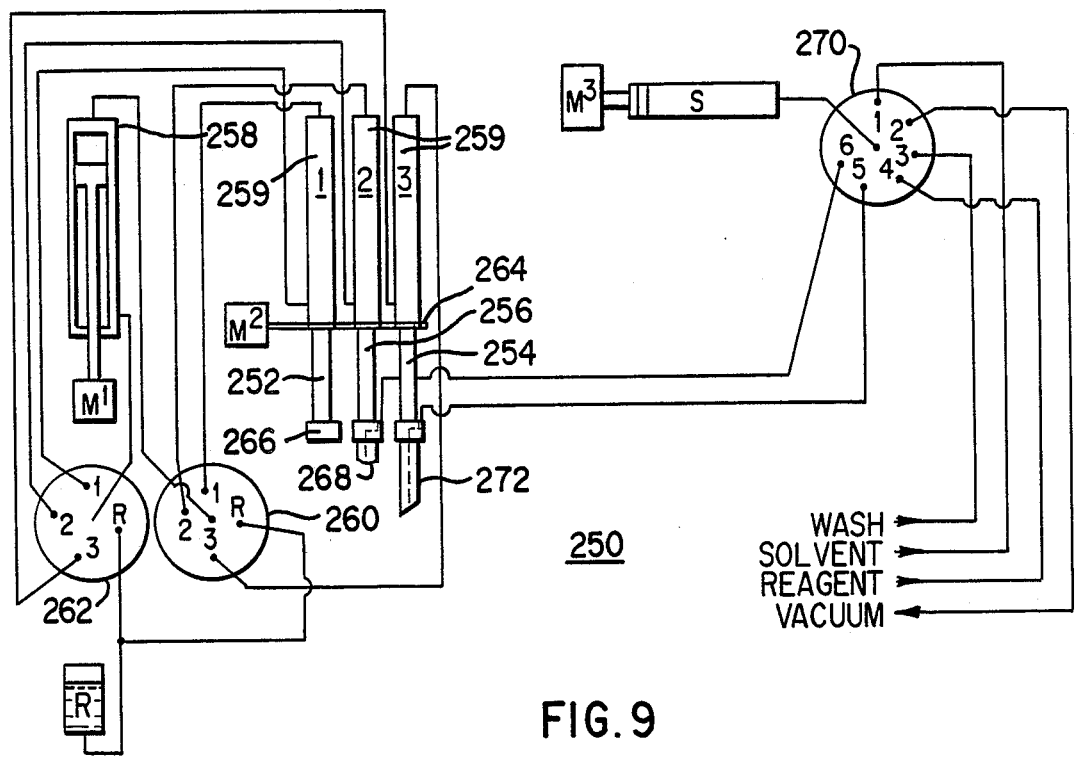
FIG. 9 is a schematic view of an apparatus which can be used for the preprogrammed, automatic or semi-automatic preparation of a sample for analysis in the container of FIG. 8.

Schematically shown in FIG. 9 is an apparatus, generally 250, which can be used for automatically or semi-automatically preparing samples for analysis in the container 210 of FIG. 8 by a procedure which can involve rotating the magazine 213 about its central vertical axis. The apparatus 250 includes three manipulating probes 252, 254 and 256 which are arranged in a row and each of which is vertically aligned. The probes 252, 254 and 256 can be positioned above the container 210 and can be raised and lowered hydraulically into different chambers A-G of the container 210 by means of a conventional master hydraulic cylinder 258 that is powered by a conventional first stepper motor M1. The master cylinder 258 is connected to three conventional dependent hydraulic cylinders 259, each of which is connected to, and controls the vertical movement of, a different one of the probes 252, 254 and 256. The master cylinder 258 also is connected to a conventional hydraulic fluid reservoir R. The fluid connections between the master cylinder 258 and the dependent cylinders 259 and the reservoir R are governed by a pair of conventional, multi-position, high pressure control valves 260 and 262. The probes 252, 254 and 256 and their dependent cylinders 259 are preferably mounted on a generally horizontal support structure 264 which can be rotated by a second conventional stepper motor M2 about the central vertical axis of the middle probe 256. When one or both of the outer probes 252 and 254 are inserted into the peripheral chambers A-F of its axis in a controlled manner by rotation of the inserted probes about the axis of the middle probe 256 powered by the second motor M2.

The lower end of each probe 252-256 is adapted to be inserted downwardly into one of the chambers A-G of the disposable container 210 of FIG. 8, through the open mouth 231 thereof. If desired, the bottom of each probe can be the same, but preferably, the bottom of each probe is different so that each can perform a different function when inserted into one of the chambers A-G. The support structure 264 for the probes 252-256 is preferably adapted to be rotated 360° about the axis of the middle probe 256 by the second motor M2 so that each of the outer probes 252 and 254 can be inserted into any of the peripheral chambers A–F of the container 210.

As shown in FIG. 9, one of the outer probes 252 can have a plunger rod 266 at its bottom. The plunger 266 has the same cross-sectional area as each of the peripheral chambers A–F of the container 210 and can be used for forcing the contents of one peripheral chamber, below the probe 252, downwardly into a second chamber via the openings and channels in the top of the valve 220 by moving the probe 252 downwardly in the one chamber. The center probe 256 can have a filling tube 268 at its bottom which can be used for filling the center chamber G of the container 210 with a sample to be prepared for analysis. If desired, the filling tube 268 can also be used for adding a wash liquid, a solvent or a reagent to the center chamber G. To carry out its functions, the filling tube 268 can be connected to a third conventional, multi-position, control valve 270 which is connected to sources of wash liquid, solvent and reagent, as well as the samples to be analyzed. In this regard, the source of samples, that is connected to the apparatus 250 and its third control valve 270, can be a conventional syringe S which can be actuated by a third conventional stepper motor M3 connected to the syringe. The other outer probe 254 can have a needle 272 at its bottom that is adapted to be inserted into one of the peripheral chambers A–F of the container 210. The needle 272 can be used to withdraw liquid samples, by vacuum, from a peripheral chamber A–F, as well as add a wash liquid, solvent or reagent to one of the peripheral chambers A–F. To carry out its functions, the needle 272 can also be connected to the third valve 270, and the third valve can, in turn, be connected to a source of vacuum. The source of vacuum, connected to the third valve 270, can be connected, in turn, to another control valve (not shown) which is connected to: (a) apparatus for disposal and recycling of waste material withdrawn from the container 210 of FIG. 8; and (b) automatic or semi-automatic analysis equipment adapted to receive a sample prepared for analysis in the chambers A–F of the container 210.

In the apparatus 250 of FIG. 9, the operations of the stepper motors M1, M2 and M3 and the control valves 260, 262 and 270, which control the hydraulic cylinders 258 and 259 and the plunger 266, filling tube 268 and needle 272, can be pre-programmed and automatically controlled in a conventional manner so that they operate automatically to prepare a sample for analysis in the disposable container 210 of FIG. 8. The probes 252, 254 and 256 can be sequentially inserted into the mouths 231 of the chambers A–G in the container 210 when the container is positioned beneath the probes by automatically: (a) activating the first stepper motor M1 connected to the master cylinder 258 so that hydraulic pressure is supplied to the dependent cylinders 259; and (b) setting the first and second control valves 260 and 262 so that the master cylinder 258 is connected to the tops of the dependent cylinders 259 and the reservoir R is connected to the bottoms of the dependent cylinders to lower the individual probes 252-256. Then, a sample, wash liquid, solvent and/or reagent can be added to, or withdrawn from, the various chambers A–G in any desired sequence by automatically activating the third motor M3 and/or regulating the position of the third valve 270. During the preparation of a sample for analysis, the magazine 213 of the container 210 also can be rotated about its central vertical axis relative to the distributor valve 220 by automatically activating the second motor M2 to rotate the support structure 264 about the central vertical axis of the central probe 256 whereby the outer probes 252 and 254 urge the peripheral chambers A–F, in which they are inserted, to rotate about the central chamber G. After utilizing the outer probes 252 and 254 for rotating the magazine 213, the probes can be automatically withdrawn from the chambers A–G by automatically: (a) activating the first stepper motor M1 so that the master cylinder 258 supplies hydraulic pressure to the dependent cylinders 259; and (b) setting the control valves 260 and 262 so that the master cylinder 258 is connected to the bottoms of the dependent cylinders 259 and the reservoir is connected to the tops of the dependent cylinders to raise the individual probes 252–256. Thereafter, the outer probes 252 and 254 can be rotated as described above to position these probes above different peripheral chambers A–F and then can be reinserted into the different chambers as described above to perform different or additional sample preparation operations.

It is thought that the invention and many of its attendant advantages will be understood from the foregoing description of the disposable sample preparation containers 10, 110 and 210, and it will be understood that various changes can be made in their construction without departing from the spirit and scope of the invention or sacrificing all of its material advantages, the embodiments hereinbefore described being merely preferred embodiment. For example, one or more channels 36 in valve 20 of container 10 of FIGS. 1–4 can be provided with additional openings 38 between the ends of the channels, so that each channel can provide fluid flow communication between the ports 30 of more than two chambers A–F. Alternatively, one or more channels 36 in valve 20 of container 10 can be so configured that the openings 38 in the ends of the channels 36 provide fluid flow communication through the channels 36 between the ports 30 of chambers A–F which are not adjacent to one another about the central vertical axis of the magazine 13. Furthermore, the sample preparation chambers A–G of the containers 10, 110 and 210 of FIGS. 1–8 need not be generally cylindrical but are preferably vertically elongated. Also, all the mouths 31, 131 and 231 on top of the chambers A–G of the containers 10, 110 and 210 need not be open, and preferably one or more of the mouths will be closed with a conventional removable sealing member, such as a covering of foil or plastic film. Also, one or more of the chambers A–G will preferably be provided with a conventional flotation plug which can float upon, and thereby cover, any liquid entering the ports 30, 130 or 230 at the bottoms of the chambers to reduce evaporation and prevent the liquid from overflowing the chamber through its open mouth 31, 131 or 231.

I claim:
1. A sample preparation apparatus comprising:
a disposable sample preparation container having a top and a bottom, said container comprising,
a magazine having a top and a bottom located in the container,
and having a vertical axis,
a plurality of independent sample holding and preparation chambers in the magazine, spaced about said axis; each chamber including means defining a mouth at a top thereof near the top of the magazine and means defining a port at a bottom thereof near the bottom of the magazine, and having a volume sufficient for temporary sample storage, at least one of said mouths being free of fixed fluid communication means; and a distributor valve positioned beneath the magazine; said valve including a top and a bottom; and said distributor valve including at least one fluid flow communication channel that extends between means defining at least two openings in said top of the valve; each of said at least two openings being adapted to establish fluid flow communication between the channel and a port of one of said plurality of chambers of the magazine when one of the openings is located beneath the port;

the valve and the magazine being rotatable relative to one another about the axis of the magazine, so that said at least two openings in the top of the valve can be aligned beneath the ports of different combinations of chambers to provide fluid flow communication between such different combinations of chambers through the channel.

2. The container of claim 1 wherein the magazine is generally cylindrical and is constructed and arranged to be rotated about its central vertical axis and the valve is adapted to be held to prevent it from rotating about the axis of the magazine, by provision of means for holding the valve on the bottom thereof so as to prevent rotation of the valve about the axis of the magazine with rotation of the magazine.

3. The container of claim 1 wherein the magazine is generally cylindrical and is constructed and arranged to be rotated about its central vertical axis and the valve is adapted to be held to prevent it from rotating about the axis of the magazine, and wherein a housing is provided about the magazine and valve; and means are provided between the housing and magazine for retaining the magazine within the housing but allowing the magazine to rotate about its central vertical axis within the housing; and means are provided between the housing and valve for preventing the valve from rotating within the housing with rotation of the magazine.

4. The container of claim 3, wherein the means for preventing the valve from rotating comprises mating male and female detent members between the valve and the housing and the means for retaining the magazine within the housing comprises an annular key and mating keyway between the magazine and housing.

5. The container of claim 1, wherein the chambers are equally spaced about the central vertical axis of the magazine.

6. The container of claim 5, wherein the valve has a plurality of fluid flow communication channels therein;
each channel including a pair of openings in the top of the valve; the pair of openings of each channel being constructed and arranged to establish fluid flow communication between the channel and the ports of two of said plurality of chambers which are adjacent to one another about a central vertical axis of the magazine.

7. The container of claim 1, wherein a housing is provided about the magazine and the valve, and the valve is supported atop a generally annular, inwardly extending ledge portion of the housing.

8. The container of claim 7, wherein a generally circular aperture, defined by the annular ledge portion of the housing, is formed for allowing access to the bottom of the valve.

9. The container of claim 8, wherein means are provided on the bottom of the valve for rotating the valve within the housing about the axis of the magazine.

10. The container of claim 9, wherein means are provided between the housing and the magazine for retaining the magazine within the housing and preventing the magazine from rotating within the housing with the valve.

11. The container of claim 1 in which there are tow ports in simultaneous alignment with separate openings in the top of the valve for continuous fluid flow in and out of the chamber by way of said two ports.

12. A sample preparation apparatus comprising:
a disposable sample preparation container having a top and a bottom, said container comprising,
a magazine having a top and a bottom, and having a vertical axis,
a plurality of independent sample holding and preparation chambers in the magazine, spaced about said axis; each chamber including means defining a mouth at a top thereof near the top of the magazine and means defining a port at a bottom thereof near the bottom of the magazine, and having a volume sufficient for temporary sample storage,
and
a distributor valve positioned beneath the magazine, said valve including a top and a bottom; and
said distributor valve including at least one fluid flow communication channel that extends between at least two of said ports at the bottom of said chambers;
the valve and the magazine being rotatable relative to one another about the axis of the magazine, so that said communication channel can be aligned beneath the ports
of different combinations of chambers to provide fluid flow communications between such difference combinations of chambers through the channel.

13. Apparatus for preparing samples for analysis in a container having a plurality of sample holding and preparation chambers having means defining open upper mouths and means defining bottom ports, a distributor valve positioned beneath the chambers and including at least one fluid flow communication channel to communicate with the respective ports of at least two of said preparation chambers, the distributor valve and the container being slidable relative to one another for aligning said at least one fluid flow communication channel between the respective ports of different ones of said chambers and including means for sliding one of said valve and said container relative to one another.

14. Apparatus set forth in claim 13 in combination with a probe, and a mechanism engaging said probe to move said probe to a respective chamber mouth.

15. Apparatus set forth in claim 14 wherein said mechanism comprises an hydraulic cylinder to move said probe into a respective chamber.

16. Apparatus in accordance with claims 14 or 15 and further comprising a plurality of probes and a plurality of mechanisms each engaging respective ones of said probes to permit selective movement of said probes.

17. Apparatus for preparing samples for analysis in a container having a plurality of sample holding and preparation chambers having means defining upper mouths and means defining bottom ports, said container having a vertical axis and said plurality of preparation chambers being arranged about said axis, a distributor valve positioned beneath said container and having a vertical axis aligned with the vertical axis of said container, at least one fluid flow communication channel to communicate with the respective ports of at least two of said preparation chambers in said container, the distributor valve and the container being rotatable relative to one another for aligning said at least one fluid flow communication channel between the respective ports of different ones of said chambers to provide fluid communication between said ports and means for rotating at least one of said valve and said container.

18. Apparatus in accordance with claim 17 wherein said means for rotating comprises a movable member having a probe movably mounted thereon for movement of said probe into and out of a respective chamber mouth.

19. Apparatus in accordance with claim 18 in which a plurality of probes are movably mounted on said movable member.

20. Apparatus in accordance with claims 18 or 19, wherein at least one probe is formed as a plunger to expel fluid from a chamber of said container.

21. Apparatus in accordance with claims 18 or 19, wherein at least one probe is formed as a hollow needle or a tube.

22. Apparatus in accordance with claims 18 or 19 wherein a plurality of said probes are movably mounted on said movable member for movement parallel to the vertical axis of said container, and one of said probes is concentric with the vertical axis of said container.

23. Apparatus in accordance with claims 17, 18 or 19 wherein drive means are drivingly connected to said means for rotating at least one of said valve and said container.

24. Apparatus in accordance with claims 18 or 19 further comprising drive means drivingly engaging a probe to move it vertically into and out of a respective chamber of said container.

25. Apparatus in accordance with claims 18 or 19 and further comprising a first drive means drivingly connected to said movable member to rotate it about said vertical axis of said magazine and a second drive means drivingly connected to at least one probe to move said at least one probe into and out of a respective chamber of said container.

* * * * *

UNITED STATES PATENT AND TRADEMARK OFFICE
CERTIFICATE OF CORRECTION

PATENT NO. : 4,889,692
DATED : December 26, 1989
INVENTOR(S) : Marc E. Holtzman

It is certified that error appears in the above-identified patent and that said Letters Patent is hereby corrected as shown below:

Column 10, line 11, "tow" should be --two--.

Signed and Sealed this

Sixteenth Day of October, 1990

Attest:

HARRY F. MANBECK, JR.

*Attesting Officer*  *Commissioner of Patents and Trademarks*